United States Patent [19]
d'Appollonia et al.

[11] Patent Number: 5,509,292
[45] Date of Patent: Apr. 23, 1996

[54] PROCESS AND APPARATUS FOR FURNISHING GAS TO A HIGH SENSITIVITY ANALYZER

[75] Inventors: Sylvain S. d'Appollonia, Guyancourt; Maurice Molozay, Le Mesnil Saint Denis, both of France

[73] Assignee: L'Air Liquide, Societe Anonyme Pour L'Etude et L'Exploitation des Procedes Georges Claude, Paris Cedex, France

[21] Appl. No.: 898,192

[22] Filed: Jun. 12, 1992

[30] Foreign Application Priority Data

Jun. 12, 1991 [FR] France ............................. 91 07139

[51] Int. Cl.⁶ ............................................. G01N 31/00
[52] U.S. Cl. ....................................................... 73/1 G
[58] Field of Search ............................ 73/1 G; 137/89, 137/592, 597, 599, 605

[56] References Cited

U.S. PATENT DOCUMENTS 4,269,057  5/1981  Ong et al. ................................. 73/1 G
4,385,910  5/1983  Eilers et al. .............................. 73/1 G

FOREIGN PATENT DOCUMENTS 0370151  5/1990  European Pat. Off. .
0370870  5/1990  European Pat. Off. .
60-66142  4/1985  Japan .

OTHER PUBLICATIONS

"The Technique of Producing Reference-Standard Gas by the Flow-Measuring Method", *Measurement*, vol. 1, No. 4, Oct.–Dec. 1983, by H. Uchiyama et al., pp. 172–176.

*Primary Examiner*—Robert Raevis
*Attorney, Agent, or Firm*—Young & Thompson

[57] ABSTRACT

A primary flow (Q) of a carrier gas is divided into a series of flows of predetermined flow rate ($q_1$–$q_{10}$). There is introduced into a first of these flows ($q_1$) a predetermined quantity of gas (A) to be analyzed, so as to obtain a first mixture ($M_1$). This first mixture ($M_1$) is diluted with a carrier gas flow ($q_3$) to constitute a second mixture ($M_2$). A portion ($d_1$) of this second mixture is diluted with a carrier gas flow ($q_5$) to constitute a third mixture ($M_3$), and so on. A calibrating gas ($U_5$) that contains very little of the second gas is provided. These flows feed a series of outlets, usable in parallel, of controlled flow rates of different mixtures over different ranges from very low content to higher content of the gas to be analyzed. The invention is useful particularly for the calibration of high sensitivity hygrometers.

12 Claims, 2 Drawing Sheets

PROCESS AND APPARATUS FOR FURNISHING GAS TO A HIGH SENSITIVITY ANALYZER

FIELD OF THE INVENTION

The present invention relates to a process for providing, to at least one high sensitivity analyzer, small quantities of a first gas contained in a second gas, comprising the steps of dividing a primary flow of the second gas into a first flow and a second flow greater than the first flow, introducing into the first flow a predetermined quantity of the first gas to constitute a first mixture, and combining at least one portion of the second flow with the first mixture to constitute a second mixture available at a first utilization outlet to supply to the analyzer.

BACKGROUND OF THE INVENTION

Modern technology requires increasingly the ability to detect very small quantities, down to parts per billion, of a first gas and a second gas. The high sensitivity analyzers provided for this purpose have calibration problems that are difficult to solve, particularly for hygrometers. The known processes, of the type defined above, using a dilution of the first mixture with the second flow, permit covering at the utilization outlet only a limited range, the passage to another range requiring a modification of the means for injecting into the first flow the predetermined quantity of the first gas.

SUMMARY OF THE INVENTION

The present invention has for its object to provide a process permitting in a reliable, reproducible and modulatable manner, covering, with a single system which is flexible in use and not cumbersome, an enormous range of calibration at plural outlets, permitting operation at very low levels less than 0.01 ppm (parts per million), permitting rapid calibration and guaranteeing a stability of the quantity of dilution of the various output mixtures.

To do this, according to a characteristic of the invention, the process comprises the steps of dividing the second flow into a third flow, for combination with the first mixture, and a fourth flow, larger than the third flow, withdrawing a portion of the second mixture before it is supplied to the first utilization outlet, and combining at least a portion of the fourth flow with the withdrawn portion of the second mixture to constitute a third mixture available at a second utilization outlet to supply to an analyzer, the third mixture having thus a predetermined content of the first gas less than that of the first mixture available at the first utilization outlet.

More particularly, the process comprises also the stages of dividing the fourth flow into a fifth flow for combination with the withdrawn portion of the second mixture, and a sixth flow larger than the fifth flow, withdrawing a portion of the third mixture before supply to the second outlet, combining at least a portion of the sixth flow with the portion of the third mixture to constitute a fourth mixture available at a third outlet, typically dividing the sixth flow into a seventh flow, for combination with the withdrawn portion of the third mixture, and an eighth flow larger than the seventh flow, withdrawing a portion of the fourth mixture before supply to the third outlet, combining at least a portion of the seventh flow with the withdrawn portion of the fourth mixture to constitute a fifth mixture available at the fourth outlet, and preferably dividing the eighth flow into a ninth flow, for combination with the withdrawn portion of the fourth mixture, and a tenth flow, withdrawing a portion of the fourth mixture before supplying the same to the third outlet, passing the tenth flow through a separator, typically a cryogenic trap to provide a calibrating mixture, via a fifth outlet, preferably after combination with a portion of the withdrawn portion of the fourth mixture.

With such an arrangement, starting from a primary flow divided several times and with introduction of a predetermined quantity of the first gas into the second gas at a single station, there is obtained at the different utilization outlets adjustable and graduated ranges for example between 1,000 ppm and 0.01 ppm or less, two different outlets being adapted to be used in parallel for the zero calibration or the standardization of two analyzers.

The present invention also has for its object an apparatus for supplying gas to at least one high sensitivity analyzer for practicing the above process, of the type comprising a second gas source feeding a first line comprising means for introduction of the second gas, and a second line connected to the first line downstream of the introduction means and terminating in a first outlet section connectible to the analyzer, characterized in that the second line is divided into a third line connected to a first branch line from the first outlet section and ending in a second outlet section connectible to the analyzer.

More specifically, the second line is divided into a fourth line connected to a second branch line from the second outlet portion and ending in a third outlet portion, the second line typically dividing into a fifth line connected to a third branch line from the third outlet portion and ending in a fourth outlet portion connectible to the analyzer, the second line preferably being divided into a sixth line, passing through a cryogenic trap, connected to the third branch line and ending in a fifth outlet portion connectible to the analyzer.

More particularly, for use in the calibration of hygrometers, the first gas being water vapor, the introduction means is constituted by a thermostatic water level saturator preferably double walled and of controlled pressure.

BRIEF DESCRIPTION OF THE DRAWINGS

Other characteristics and advantages of the present invention will appear from the following description of an embodiment of the invention, given by way of illustration but non-limiting, with reference to the accompanying drawings, in which.

DETAILED DESCRIPTION OF THE INVENTION

Figure 1:
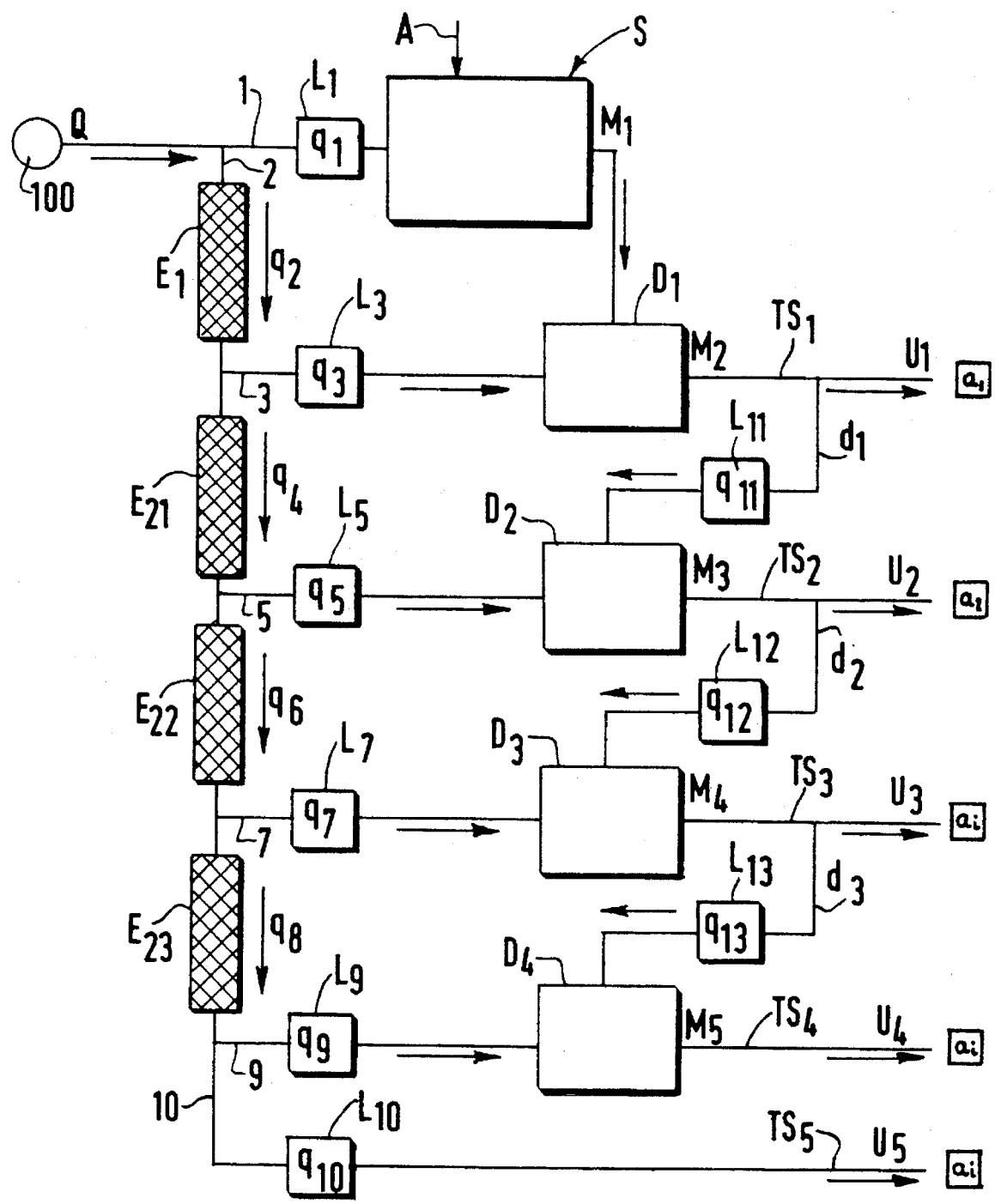
FIG. 1 is a schematic diagram of apparatus for supplying gas according to the invention.

In the description which follows and in the drawings, identical or similar elements bear the same reference numerals.

In the diagram of FIG. 1, a flow Q of a carrier gas, typically an inert gas such as nitrogen or argon, from a source 100 supplies a first line 1, comprising a station S for the introduction of a small predetermined quantity of an analysis gas A into the carrier gas flowing through the first line 1 and supplying at its outlet a first gaseous mixture M1. The source of carrier gas 100 also supplies a second line 2, provided with a first purification device $E_1$ downstream of which it is divided into a third line 3 connected, at a first dilution station $D_1$, to the first line 1 downstream of the introduction device S of the analysis gas A and terminating in a first outlet section $TS_1$ connectible at $U_1$ to an analyzer. The second line 2 extends, downstream of purifier $E_1$, through a purifier $E_{21}$ and is divided into a fifth line 5 connecting, at a second dilution station $D_2$, to a first branch line $d_1$ from the first outlet section $TS_1$ and terminating in a second outlet section $TS_2$ connectible at $U_2$ to an analyzer. The second line 2 extends through a purifier $E_{22}$ and is divided into a seventh line 7 connecting, in a third dilution station $D_3$, to a second branch line $d_2$ from the second outlet section $TS_2$, and terminating in a third outlet section $TS_3$ connectible at $U_3$ to an analyzer. The second line extends through a purifier $E_{23}$ and is divided into a ninth line 9 and a tenth line 10. The ninth line 9 is connected in a fourth dilution station $D_4$ to a third branch line $d_3$ from the third outlet section $TS_3$ and terminates in a fourth outlet section $TS_4$ connectible at $U_4$ to an analyzer. The tenth line 10 ends in a fifth outlet section $TS_5$ connectible at $U_5$ to an analyzer. The flow rates $q_1$, $q_3$, $q_5$, $q_7$, $q_9$ and $q_{10}$ in the lines 1, 3, 5, 7, 9 and 10 are determined by flow limiting means $L_1$, $L_3$, $L_5$, $L_7$, $L_9$ and $L_{10}$, respectively. Preferably, the flows $q_{11}$, $q_{12}$, $q_{13}$ in the branch lines $d_1$, $d_2$, $d_3$ are determined by flow limiting means $L_{11}$, $L_{12}$, $L_{13}$, respectively.

The purifiers $E_1$ and $E_{21}$ are purifiers of the zeolite and/or activated charcoal adsorbent type to purify carrier gas of any contaminants, water vapor, methane or $CO_2$. The different conduits are of internally electropolished stainless steel.

It will be understood that with such an arrangement, starting from a primary carrier gas flow Q and from a first predetermined mixture $M_1$ of the carrier gas and a small quantity of the gas A to be analyzed, there is obtained, at the first outlet $U_1$ a second mixture $M_2$ of the two gases with a first reduced content of gas to be analyzed, at a second outlet $U_2$ a third gaseous mixture $M_3$ with a second content lower than the first of the gas to be analyzed, and so on for the outlets $U_3$ to $U_5$, this last outlet supplying a zeroing or calibrating gas corresponding to the carrier gas containing an infinitesimally small quantity of the gas to be analyzed, typically less than 0.005 ppm, each dilution, at the stations $D_1$ to $D_4$, being carried out with the same carrier gas which is substantially pure and free from impurities, particularly of the type of those of the gas A to be analyzed. The various flow rate limiting means $L_1$ to $L_{13}$ permit guaranteeing constant predetermined flow rates to the different outlets $U_1$ to $U_5$ no matter what the uses to which these various outlets are put. Because of this, two or more of these outlets can be used, which offer different ranges, covering a wide range, of contents of gas to be analyzed, to effect the simultaneous standardization or calibration of several analyzers.

Figure 2:
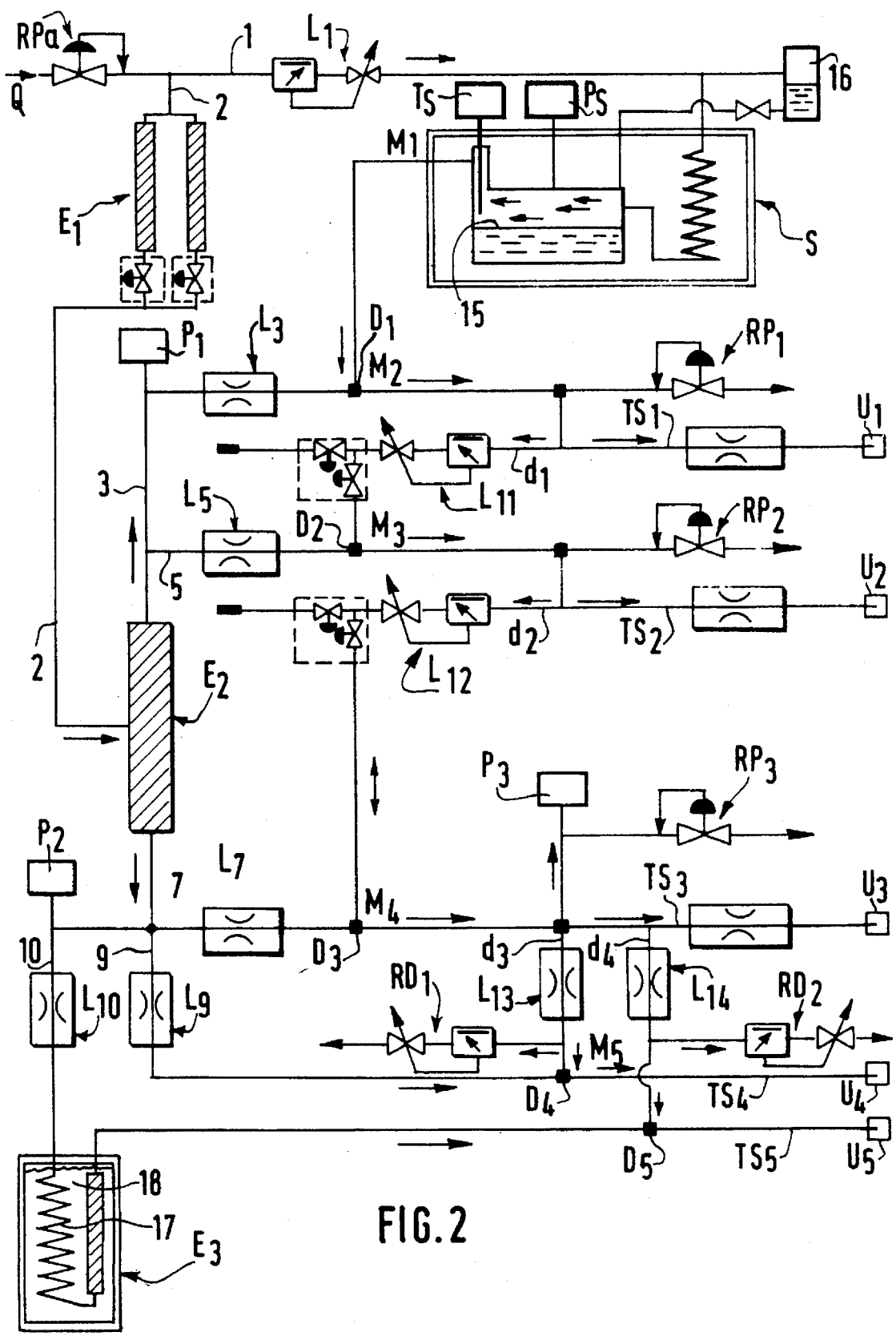
FIG. 2 is a schematic view of an installation according to FIG. 1 for the calibration and standardization of hygrometers.

There is shown in greater detail in FIG. 2 an apparatus according to the invention for use for the standardization of hygrometers. The supply pressure of the carrier gas system is ensured, upstream of the lines 1 and 2, by an upstream pressure regulator $RP_a$. In this embodiment, the gas A to be analyzed being water vapor, the introduction apparatus S is here constituted by a double walled thermostatic saturator providing for the flow of gas through the first line 1 a water level 15, the body of water being contained in a water reservoir 16, the temperature and the pressure of the overhead gas above the water level 15 being adjusted to a saturation pressure $P_s$ and temperature $T_s$. To this end, the flow rate limiting means $L_1$ in the line 1 is here constituted by a flow rate regulator ensuring, at the outlet of the saturator S, a constant flow rate of the initial mixture of moist gas $M_1$, which will be successively diluted by the dry carrier gas at dilution stations $D_1$ to $D_5$. In this embodiment, the tenth line 10 comprises a purifier $E_3$ constituted by a cryogenic trap with heat exchanger 17 in a liquid nitrogen bath 18 and the tenth line 10 is connected, in a fifth dilution station $D_5$, to a fourth branch line $d_4$ coming, as does the third branch line $d_3$, from the third output section $TS_3$ connected to the third outlet $U_3$, the fourth branch line $d_4$ being provided with flow rate limiting means $L_{14}$. Typically, the flow rate limiting means $L_3$, $L_5$, $L_7$, $L_9$, $L_{10}$, $L_{13}$ and $L_{14}$ are constituted by sonic throat fixed restrictors while the flow rate limiters $L_{11}$ in the first branch line $d_1$ and $L_{12}$ in the second branch line $d_2$ are constituted by controllable flow rate regulators.

Preferably, according to one aspect of the invention, upstream of the restrictors $L_{13}$ and $L_{14}$ in the branch lines $d_3$ and $d_4$, to maintain a continuous flow through all the lines of the system and to ensure precise regulation of the flow rates which will not be susceptible to variation with time, therefore to guarantee a particularly reliable quality of analysis, the output sections $TS_1$ to $TS_3$ are associated with pressure regulators $RP_1$, $RP_2$ and $RP_3$, respectively disposed in the lines of circulating flow, the excess emptying into the ambient air or into a recovery means for excess mixture, while the fourth and fifth output sections $TS_4$ and $TS_5$ are each associated with a discharge flow regulator $RD_1$ and $RD_2$ in a corresponding discharge circuit. An arrangement of this type is described in the document EP-A-0.479.633 whose content is incorporated herein by reference. Preferably, a pressure gauge $P_1$ is provided upstream of the restrictions $L_3$ and $L_5$, a pressure gauge 2 is provided upstream of the restrictions $L_7$, $L_9$ and $L_{10}$ and a pressure gauge $P_3$ is provided in the discharge line of the third output section $TS_3$, upstream of the pressure regulator $RP_3$, to detect the pressure in the third output section $TS_3$, upstream of the restrictions $L_{13}$ and $L_{14}$ in the branch lines $d_3$ and $d_4$.

By way of example, the following parameters could be adapted for the system of FIG. 2:

the carrier gas is a dry inert gas, typically nitrogen or if desired argon;

the supply flow rate Q is of the order of 15 liters per minute and the upstream pressure, fixed by the pressure regulator $RP_a$ is $8 \times 10^5$ Pa;

the flow rate $q_1$ is regulated by the flow rate regulator $L_1$ and is about 1 liter per minute and, for a saturation temperature $T_s$ between 10° and 20° C. and a saturation pressure $P_s$ between 3 and $5 \times 10^5$ pa, the water content of the mixture $M_1$ leaving the saturator is of the order of 4,000 ppm;

the flow rate $q_3$, determined by the restriction $L_3$, is of the order of 3.5 liters per minute while the flow rates $q_5$, $q_7$, $q_9$ and $q_{10}$, fixed by the restrictions $L_5$, $L_7$, $L_9$ and $L_{10}$, are of the order of 2.5 liters per minute, so as to supply the different outlets $U_1$ to $U_5$.

What is claimed is:

1. A process for providing to at least one high sensitivity analyzer ($a_i$) small quantities of a first gas (A) contained in a second gas, comprising: dividing a primary flow (Q) of the second gas into a first flow ($q_1$) and a second flow ($q_2$) greater than the first flow, introducing into the first flow ($q_1$) a predetermined quantity of the first gas (A) to constitute a first mixture ($M_1$), dividing the second flow ($q_2$) into a third flow ($q_3$) and into a fourth flow ($q_4$) larger than said third flow, combining the third flow ($q_3$) with the first mixture ($M_1$) to constitute a second mixture ($M_2$), dividing the second mixture into a first part and a second part, supplying said first part to a first utilization outlet ($U_1$) for supply to the analyzer, combining said second part with a portion of the fourth flow to constitute a third mixture ($M_3$), supplying the third mixture to a second utilization outlet ($U_2$) for supply to an analyzer, dividing the fourth flow ($q_4$) into a fifth flow ($q_5$) constituting said portion of the fourth flow for combining with the second part of the second mixture, and into a sixth flow ($q_6$) larger than said fifth flow, withdrawing a portion of the third mixture before supplying the third mixture to the second utilization outlet ($U_2$), combining at least a portion of the sixth flow with the withdrawn portion of the third mixture to constitute a fourth mixture ($M_4$), supplying said fourth mixture to a third utilization outlet ($U_3$) for supply to an analyzer, dividing the sixth flow ($q_6$) into a seventh flow ($q_7$), constituting said portion of the sixth flow for combining with the withdrawn portion of the third mixture, and into an eighth flow ($q_8$) larger than the seventh flow, withdrawing a portion of the fourth mixture before supplying the fourth mixture to the third utilization outlet ($U_3$), combining at least a portion of the eighth flow with part of the withdrawn portion of the fourth mixture to constitute a fifth mixture ($M_5$), supplying said fifth mixture to a fourth utilization outlet ($U_4$) for supply to an analyzer, dividing the eighth flow ($q_8$) into a ninth flow ($q_9$), constituting said portion of the eighth flow for combining with part of the withdrawn portion from the fourth mixture, and into a tenth flow ($q_{10}$), passing the tenth flow through a cryogenic trap, combining the tenth flow with another part of the withdrawn portion of the fourth mixture, and supplying the mixture thus formed to a fifth utilization outlet ($U_5$) for supply to an analyzer.

2. Process according to claim 1, wherein the third, the fifth, the seventh, the ninth and the tenth flows are each combined with a mixture regulated as to flow rate by a fixed restriction.

3. Process according to claim 1, further comprising the step of purifying at least one of the divided flows.

4. Process according to claim 1, further comprising the step of restricting said first flow.

5. Process according to claim 1, wherein said first gas is water vapor.

6. Process according to claim 5, further comprising the step of introducing said water vapor into the second gas by saturation of the second gas above a water level.

7. An apparatus for supplying to at least one high sensitivity analyzer small quantities of a first gas contained in a second gas comprising: a source (100) of a second gas fluidly connected to pipe means, said pipe means being divided into a first conduit (1) including means for introducing (S) a first gas (A) therein, and into a second conduit (2) upstream of said means for introducing; said second conduit communicating with a first outlet section ($TS_1$) that is connected to said means for introducing and that is connectable to an analyzer ($a_i$), said second conduit (2) being divided into a third conduit (5) connected to a first branch conduit ($d_1$) from said first outlet section and terminating in a second outlet section ($TS_2$) connectable to an analyzer, said second conduit (2) being divided also into a fourth conduit (7) connected to a second branch conduit ($d_2$) from said second outlet section ($TS_2$) and terminating in a third outlet section ($TS_3$) connectable to an analyzer, said second conduit (2) being divided into a fifth conduit (9) connected to a third branch conduit ($d_3$) from said third outlet section ($TS_3$) and terminating in a fourth outlet section ($TS_4$) connectable to an analyzer, said second conduit (2) being also divided into a sixth conduit (10) passing through a cryogenic trap ($E_3$) connected to a fourth branch conduit ($d_4$) from the third outlet section ($TS_3$) and terminating in a fifth outlet section ($TS_5$) connectable to an analyzer.

8. Apparatus according to claim 7, wherein at least one of the conduits divided from said second conduit includes at least one upstream purification device.

9. Apparatus according to claim 7, wherein each of the conduits divided from said second conduit comprises an upstream fixed flow restrictor.

10. Apparatus according to claim 7, wherein each of the conduits divided from said second conduit is provided with a device for discharging excess gas flow.

11. Apparatus according to claim 7, wherein said cryogenic trap comprises heat exchange means in a bath of liquid nitrogen.

12. Apparatus according to claim 7, wherein said first gas is water vapor, and said means for introducing is a thermostatic water level saturator.

\* \* \* \* \*